United States Patent [19]
Platz et al.

[11] Patent Number: 6,019,968
[45] Date of Patent: Feb. 1, 2000

[54] DISPERSIBLE ANTIBODY COMPOSITIONS AND METHODS FOR THEIR PREPARATION AND USE

[75] Inventors: Robert M. Platz, Half Moon Bay; John S. Patton, San Carlos; Linda C. Foster, Mountain View, all of Calif.; Mohammed Eljamal, Tripoli, Lebanon

[73] Assignee: Inhale Therapeutic Systems, Inc., San Carlos, Calif.

[21] Appl. No.: 08/951,312

[22] Filed: Oct. 16, 1997

Related U.S. Application Data

[63] Continuation-in-part of application No. 08/423,515, Apr. 14, 1995, and application No. PCT/US96/05070, Apr. 12, 1996.

[51] Int. Cl.$^7$ ................................................. A61K 39/395
[52] U.S. Cl. ........................................................ 424/130.1
[58] Field of Search ................................ 514/535, 171, 514/130.1

[56] References Cited

U.S. PATENT DOCUMENTS

| | | | |
|---|---|---|---|
| 4,305,925 | 12/1981 | Kapmeyer | 436/509 |
| 5,354,562 | 10/1994 | Platz et al. | 424/489 |
| 5,458,135 | 10/1995 | Patton et al. | 128/200.14 |

FOREIGN PATENT DOCUMENTS

| | | |
|---|---|---|
| WO96/09085 | 3/1996 | WIPO . |
| WO97/41833 | 11/1997 | WIPO . |

OTHER PUBLICATIONS

Brown, Alan R., et al., "Chamber for Testing Metered–Dose Propellant Driven Aerosols for Immunologically Relevant Proteins", *J. Immuno. Meth.*, 176:203–212 (1994).

Brown, Alan R., "Propellant–Driven Aerosols of Proteins", *Aerosol Sci. Tech.*, 24:45–56 (1996).

Gombotz, Wayne R., et al., The Stabilization of a Human IgM Monoclonal Antibody with Poly(vinylpyrrolidone), *Pharm. Res.*, 11:624–632 (1994).

Maruyama, Kazuo, et al., "Tragetability of Novel Immunoliposomes Modified with Amphipathic Poly(ethylene Glycol)s conjugated at Their Distal Terminals to Monoclonal Antibodies", *Biochimica et Biophysica Acta*, 1234:74–80 (1995).

Paborji, Mehdi, et al., "Chemical and Physical Stability of Chimeric L6, a Mouse–Human Monoclonal Antibody", *Pharm. Res.*, 11(5):764–771 (1994).

Piazza, Franco M., et al., "Immunotherapy of Respiratory Syncytial Virus Infection in Cotton Rats (*Sigmodon fulviventer*) Using IgG in a Small–Particle Aerosol", *J. Infec. Dis.*, 166:1422–1424 (1992).

Singh, Brahm Pal, et al., "Heat Aggregation Studies of Phycobilisomes, Ferritin, Insulin, and Immunoglobulin by Dynamic Light Scattering", *Biopolymers*, 31:1387–1396 (1991).

*Primary Examiner*—Jose' G. Dees
*Assistant Examiner*—Alton Pryor
*Attorney, Agent, or Firm*—Burns, Doane, Swecker & Mathis, L.L.P.

[57] ABSTRACT

This invention relates to dispersible antibody compositions and methods for preparing and using these compositions. In particular, the present invention relates to dry powder dispersible antibody compositions wherein antibody conformation is preserved. The compositions have good powder dispersibility and other desirable characteristics for pulmonary delivery of therapeutic antibodies.

13 Claims, 4 Drawing Sheets

DISPERSIBLE ANTIBODY COMPOSITIONS AND METHODS FOR THEIR PREPARATION AND USE

CROSS REFERENCE TO RELATED APPLICATIONS

This application is a continuation-in-part of U.S. application Ser. No. 08/423,515 filed Apr. 14, 1995 and PCT Application No. PCT/US96/05070 filed Apr. 12, 1996, which applications are incorporated by reference herein in their entirety.

FIELD OF THE INVENTION

This invention relates to dispersible antibody compositions and methods for preparing and using these compositions. In particular, the present invention relates to dry powder dispersible antibody compositions wherein antibody conformation is preserved. The compositions have good powder dispersibility and other desirable characteristics for pulmonary delivery of therapeutic antibodies.

BACKGROUND OF THE INVENTION

The protective effects of humoral immunity are known to be mediated by a family of structurally related glycoproteins called antibodies. Antibodies initiate their biological activity by binding to antigens. Antibody binding to antigens, which may be covalent or non-covalent, is exquisitely specific for one antigen and is often very strong.

Antibodies are produced in a membrane-bound form by B-lymphocytes. Blood contains many different antibodies, each derived from a clone of B-cells and each having a distinct structure and specificity for antigen. Antibodies are present in the cytoplasmic compartment and on the surface of B-lymphocytes, in the plasma, in interstitial fluid of the tissues and in secretory fluids such as saliva and mucous. Surfaces of immunoeffector cells, such as mononuclear phagocytes, natural killer cells and mast cells also have antibodies.

All antibodies are similar in their overall structure, accounting for certain similarities in physiochemical features such as charge and solubility. All antibodies have a common core structure of two identical light chains, each about 24 kilodaltons, and two identical heavy chains of about 55–70 kilodaltons each. One light chain is attached to each heavy chain, and the two heavy chains are attached to each other. Both the light and heavy chains contain a series of repeating homologous units, each of about 110 amino acid residues in length which fold independently in a common globular motif, called an immunoglobulin (Ig) domain. The region of an antibody formed by the association of the two heavy chains is hydrophobic. Antibodies, and especially monoclonal antibodies, are known to cleave at the site where the light chain attaches to the heavy chain when they are subjected to adverse physical or chemical conditions. Because antibodies contain numerous cysteine residues, they have many cysteine-cysteine disulfide bonds. All Ig domains contain two layers of beta-pleated sheets with three or four strands of anti-parallel polypeptide chains.

Despite their overall similarity, antibody molecules can be divided into a small number of distinct classes and subclasses based on physiochemical characteristics such as size, charge and solubility, and on their behavior in binding to antigens. In humans, the classes of antibody molecules are: IgA, IgD, IgE, IgG and IgM. Members of each class are said to be of the same isotype. IgA and IgG isotypes are further subdivided into subtypes called $IgA_1$, $IgA_2$ and $IgG_1$, $IgG_2$, $IgG_3$ and $IgG_4$. The heavy chains of all antibodies in an isotype share extensive regions of amino acid sequence identity, but differ from antibodies belonging to other isotypes or subtypes. Heavy chains are designated by the letters of the greek alphabet corresponding to the overall isotype of the antibody, e.g., IgA contains $\alpha$, IgD contains $\delta$, IgE contains $\epsilon$, IgG contains $\gamma$, and IgM contains $\mu$ heavy chains. IgG, IgE and IgD circulate as monomers, whereas secreted forms of IgA and IgM are dimers and pentamers, respectively, stabilized by the J chain. Some IgA molecules exist as trimers.

There are $1\times10^7$, and perhaps as many at $10^9$, structurally different antibody molecules in every individual, each with the unique amino acid sequence in their antigen combining sites. Sequence diversity in antibodies is confined to three short stretches within the amino terminal domains of the heavy and light chains. The amino acid sequences of the amino terminal domains are called variable (V) regions, to distinguish them from the more conserved constant (C) regions.

Antibodies have several known therapeutic applications. For example, they may be used to bind to and block cell markers and receptors. Antibodies to microorganisms may be used to inhibit or inactivate the microorganism and/or prevent or treat disease conditions caused by these microorganisms. When antibodies bind to microorganisms, they enhance their recognition and destruction by macrophages. Antibodies may be used as anticytokines, antichemokines, antihormones, antiinflammatories and immunosuppressors or as antineutrophil adhesion agents. Antibodies, especially monoclonal antibodies, may be used systemically to deliver therapy. In these cases antibodies are often used as immunoconjugates, immunoliposomes or immunomicrospheres. Antibodies can be used as apoptosis stimulators and as recognizers of cancerous and precancerous cells. Known examples of antibodies which may be useful therapeutically include the following.

MedImmune Inc. is studying the use of humanized anti-RSV monoclonal antibodies and markets a polyclonal anti-RSV antibody from donor blood (RespiGam) to treat respiratory syncytial virus (RSV) infections. MedImmune also markets CytoGam, an anti-CMV (cytomegalovirus) human immune globulin for the treatment of CMV infection. IDEC and Genentech are jointly performing clinical trials of a chimeric mouse-human monoclonal antibody (rituximab) aimed at the CD20 antigen found on mature B cells and most non-Hodgkin's lymphoma tumors for use in treating relapsed or refractory low-grade non-Hodgkin's lymphoma. GalaGen is studying the use of the polyclonal antibody Diffistat-G for treatment of *Clostridium difficile* antibiotic associated diarrhea. Smith Kline and Schering Plough are developing an anti-IL-5 antibody which has been shown in clinical trials to prevent eosinophilic inflammation and airway constriction. An anti-IgE antibody is being developed by Genentech to "switch-off" allergies. Monoclonal antibody Rhu-Mab-E25, which is a humanized chimeric $IgG_1$ monoclonal antibody for a unique epitope on human high affinity IgE receptors (FceRI), has been shown to reduce free IgE levels after the first administration by injection. It attenuated both early and late phase responses to inhaled allergens after multiple injections. Examples of antibodies used therapeutically also include a nebulized IgG (Sandoz), which is used intranasally against respiratory syncytial virus (RSV); HNK20 (Oravax), an anti-RSV IgA; and 4B9 (Bristol Myers-Squibb), an anti-group B Streptococcus IgM monoclonal antibody. Other therapeutically useful antibodies include anti-CD4 antibodies, anti-IL-2 antibodies and anti-IL-4 antibodies.

The immunotherapy of respiratory syncytial virus infection using small particle aerosols of IgG has been disclosed by Piazza et al. (The Journal of Infectious Diseases, Vol. 166, pp. 1422–1424, 1992) In this study it was shown that a 15-minute exposure to an aerosolized 5% solution of IgG effected a 50-fold reduction in pulmonary virus. Brown (Aerosol Science and Technology, Vol. 24, pp. 45–56, 1996) discloses the use of antibodies as inhibitors or antagonists of cytokines to depress respiratory inflammatory diseases or allergen-induced asthmatic responses. Also disclosed is local respiratory delivery of pathogen-specific antibody for treatment of acute viral or bacterial respiratory infections. Antibody liposomes, i.e., immunoliposomes, are disclosed by Maruyama et al. in Biochemica et Biophysica Acta, Vol. 1234, pp. 74–80, 1995. Coating liposomes with antibody leads to enhanced uptake of the immunoliposome by the reticuloendothelial system. Human monoclonal antibodies are known to be useful as antitumor agents. A mouse/human monoclonal IgG, antibody specific for the Lewis Y antigen found on the surface of tumor cells is disclosed by Paborji et al. (Pharmaceutical Research, Vol. 11, No. 5, pp. 764–771, 1994). The use of antibodies in metered-dose propellant driven aerosols for passive antibody aerosol therapy against respiratory infections is disclosed in Brown et al. (Journal of Immunological Methods, Vol. 176, pp. 203–212, 1994). Immune responses in the respiratory tract are of great importance for protection against infections of the respiratory system and for their involvement in respiratory allergies and asthma. Effective targeting of immunomodulating reagents including antibodies to the respiratory tract is shown to be of benefit in increasing local immunity to respiratory pathogens or decreasing immune mediated respiratory pathology. Inhaled immunoconjugates, immunoliposomes or immunomicrospheres have application in the lung as killers of cancer cells (immunoconjugates) or, in the case of immunoliposomes and microspheres, as stealth delivery particles of a variety of therapeutic agents. An IgM anti-group B Streptococcus monoclonal antibody is disclosed by Gombotz et al. (Pharmaceutical Research, Vol. 11, pp. 624–632, 1994).

Over the years certain drugs have been sold in compositions suitable for forming a drug dispersion for oral inhalation (pulmonary delivery) to treat various conditions in humans. Such pulmonary drug delivery compositions are designed to be delivered by inhalation by the patient of the drug dispersion so that the active drug within the dispersion can reach the lung. It has been found that certain drugs delivered to the lung are readily absorbed by the alveolar region directly into the blood circulation. Pulmonary delivery is particular promising for delivery of macromolecules such as proteins, polypeptides, high molecular weight polysaccharides and nucleic acids, which are difficult to deliver by other routes of administration. Such pulmonary delivery can be effective both for systemic delivery and for localized delivery to treat diseases of the lungs.

Pulmonary drug delivery can itself be achieved by different approaches, including liquid nebulizers, aerosol-based metered-dose inhalers (MDI's) and dry powdered dispersion devices. Chlorofluorocarbon (CFC) based MDI's are losing favor because of their adverse effect on the environment. Dry powder dispersion devices, which do not rely on CFC aerosol technology, are promising for delivering drugs that may be readily formulated as dry powders. Many otherwise labile macromolecules may be stably stored as lyophilized or spray dried powders, either by themselves or in combination with suitable powder carriers.

The ability to deliver pharmaceutical compositions as dry powders, however, is problematic in certain respects. The dosage of many pharmaceutical compositions is often critical, so it is desirable that dry powder delivery system be able to accurately, precisely and reliably deliver the intended amount of drug. Moreover, many pharmaceutical compositions, including antibodies, are quite expensive. Thus, the ability to efficiently formulate, process, package and deliver the dry powders with minimal loss of drug is critical. While the permeability of natural macromolecules in the lung is well known, combined inefficiency of macromolecule production processes and macromolecule delivery has limited commercialization of dry macromolecule powders for pulmonary delivery. It is also essential that dry powders for pulmonary delivery be readily dispersible prior to inhalation by the patient in order to assure adequate distribution and systemic absorption.

An important requirement for hand held and other powder delivery devices is efficiency. It is important that the delivered dose be relatively high to reduce the number of breaths required to achieve a total dosage. The ability to achieve both adequate dispersion and small dispersed volumes is a significant technical challenge that requires in part that each unit dosage of the powder composition be readily and reliably dispersible. Certain pulmonary delivery devices, such as those disclosed in U.S. Pat. No. 5,458,135 and International Patent Publication WO96/09085 are useful for pulmonary delivery of dry powder drugs.

Spray drying is a conventional chemical processing operation used to produce dry particulate solids from a variety of liquid and slurry starting materials. The use of spray drying for the formulation of dry powder pharmaceuticals is known but has usually been limited to small molecule and other stable drugs which are less sensitive to thermal degradation and other rigorous treatment conditions. The use of spray drying for the preparation of biological macromolecule compositions, including antibodies, can be problematic since such macromolecules are often labile and subject to degradation when exposed to high temperatures and other aspects of the spray drying process. Excessive degradation of the macromolecules can lead to drug formulations lacking in the requisite purity.

It can also be difficult to control particle size and particle size distribution in compositions produced by spray drying. For pulmonary delivery it is critical that the average particle size be maintained in a respirable range and that the amount of the composition comprising particles outside the target size range be minimized. Moreover, it can sometimes be difficult to achieve a desired low moisture content required for physical and chemical stability in the final particulate product, particularly in an economic manner. Finally, and perhaps most importantly, it has been difficult to produce the small particles necessary for pulmonary delivery in an efficient manner. For high value macromolecular drugs, high collection efficiencies, i.e., the amount of particulate drug recovered from the process in a usable form, are important. While spray drying has been used to prepare powders of macromolecules in laboratory scale equipment, commercial spray dryers are not designed to produce powders in the pulmonary size range. The methods for atomization, drying powder and collection must be modified to economically produce a protein powder with the desired product characteristics for pulmonary delivery and in sufficient yield and at commercially acceptable production rates, i.e., in excess of 30 grams per hour. Useful methods are disclosed, for example, in International Patent Application No. PCT/US97/07779, the disclosure of which is incorporated herein by reference in its entirety.

SUMMARY OF THE INVENTION

The present invention provides dispersible dry powder antibody compositions and methods for their preparation and use. These dispersible dry powder antibody compositions have a moisture content of less than about 10% by weight (% w) water, usually about 1–5% by weight, and preferably less that about 3% by weight of water. They have a particle size of about 0.1 to 7 μm mass median diameter (MMD), usually about 0.4 to 5 μm MMD, preferably about 1 to 4 μm and most preferably about 1–3 μm MMD. The dispersible dry powder antibody compositions of the present invention result in a delivered dose of greater than about 30%, usually greater than about 40%, preferably greater than about 50% and most preferably greater than about 60%. They have an aerosol particle size distribution of about 1–5 μm mass median aerodynamic diameter (MMAD), usually about 1.5–4.5 μm MMAD and preferably about 1.5–4.0 μm MMAD, or with at least about 40% (preferably at least about 50%) of the particles less than about 3.3 μm in diameter. The compositions contain at least about 40% by weight antibody. Further, the antibodies in these compositions are not aggregated and are present in their native conformation so as to retain their biological activity.

According to the present invention, antibody containing compositions having improved characteristics which overcome at least some of the deficiencies noted above with respect to prior compositions are provided. The present invention provides compositions and methods which provide a predetermined concentration of antibody, and, optionally, other excipients as a dry dispersible powder. The antibody is optionally formulated prior to spray drying with compatible excipients such as sugars, buffers, salts, surfactants, polymers, other proteins and other specific stabilizing additives as needed to provide a therapeutically effective dose, inhibit degradation during drying, promote powder dispersibility and achieve acceptable physical and chemical stability of the powder at room temperature while maintaining antibody integrity.

In one aspect the invention provides dry powder compositions for pulmonary delivery comprising an antibody that is substantially in its native conformation. Such compositions retain antibody activity upon reconstitution.

In another aspect the invention provides antibody-based dry powder compositions which are spray dried from the antibody and, optionally, excipient, in a solvent under conditions to provide a respirable dry powder. Solvents for such mixtures may include water and ethanol.

In a yet further aspect, the invention provides methods for preventing or treating a condition by administering the dry powder antibody compositions described above.

DETAILED DESCRIPTION OF THE INVENTION

The present invention is based at least in part on the discovery that antibodies may be formulated as dispersible dry powder compositions while retaining their integrity. The dispersibility characteristics of the subject antibody based compositions means that they are more suitable for use in pulmonary delivery devices than antibody compositions prepared by other methods. The compositions of the invention are readily aerosolized and rapidly absorbed through the lungs of a host when delivered by a dry powder inhaler. Standard lyophilized antibody formulations do not consist of particles with size suitable for pulmonary delivery. In contrast, the dry powder formulations of the present invention retain antibody conformation and stability, are readily dispersible for pulmonary delivery and allow for unit dose packaging.

The invention consists of compositions comprising antibodies in dry powder dispersible formulations. The use of dry particles of a certain size range allows for delivery of antibodies to the alveolar area of the lungs. Optionally, the dry powder formulations of the present invention may contain stabilizers and excipients such as sugars, polymers and other proteins. The compositions of the present invention are useful in pulmonary dry powder drug delivery systems, including but not limited to those disclosed in U.S. Pat. No. 5,458,135 and International Patent Publication WO96/09085.

A. Definitions

As used herein the following terms have the following meanings:

The terms "dispersibility" or "dispersible" mean a dry powder having a moisture content of less than about 10% by weight (% w) water, usually below about 5% w and preferably less that about 3% w; a particle size of about 0.4 to 5 μm mass median diameter (MMD), usually about 1 to 4 μm MMD and preferably 1–3 μm MMD; a delivered dose of greater than about 30%, usually greater than about 40%, preferably greater than about 50% and most preferably greater than about 60%; and an aerosol particle size distribution of about 1–5 μm mass median aerodynamic diameter (MMAD), usually about 1.5–4.5 μm MMAD and preferable about 1.5–4.0 μm MMAD, or with at least about 40% (preferably at least about 50%) of the particles less than about 3.3 μm in diameter.

The term "non-aggregated" means that the antibody is substantially oligomer-free. This means that usually less than about 15%, preferably less than about 10% and more preferably less than about 5% of the antibody in the composition comprises covalently or non-covalently bound dimers, trimers or larger aggregates.

The term "native conformation" means that the antibody in the composition substantially retains the secondary and tertiary structure of the original state of the molecule.

The term "powder" means a composition that consists of finely dispersed solid particles that are free flowing and capable of being readily dispersed in an inhalation device and subsequently inhaled by a subject so that the particles reach the spaces of the deep lung to permit penetration into the alveoli. Thus, the powder is said to be "respirable."

The term "dry" means that the composition has a moisture content such that the particles are readily dispersible in an inhalation device to form an aerosol in the absence of a liquid propellant. This moisture content is generally below about 10% w water, usually below about 5% w and preferably less than about 3% w.

The terms "pharmaceutical excipient" or "additive" mean compounds which stabilize antibody and/or improve powder aerosol performance and stability. The types of excipients useful in the present invention include proteins such as human serum albumin (HSA), carbohydrates such as sucrose, alditols such as mannitol, salts such as sodium citrate, polymers such as PVP and Ficoll, and the like.

The term "antibody" means the structurally related glycoproteins which bind to antigens. The term antibody includes monoclonal antibodies and/or IgA, IgD, IgE, IgG and IgM isotype antibodies, including these compounds present in the form of immunoconjugates, immunoliposomes or immunospheres.

B. Compositions:

The present invention is drawn to dispersible antibody-containing dry powder compositions suitable for pulmonary delivery. The compositions comprise a therapeutically effective amount of an antibody, optionally in combination with a pharmaceutically acceptable carrier or excipient.

These dry powder compositions comprise a plurality of discrete, dry particles with an average particle size below about 7 μm, preferably in the range from 0.4–5 μm, more preferably from 1–4 μm and most preferably from 1–3 μm. The average particle size of the powder is measured as mass mean diameter (MMD). Such powders are capable of being readily dispersed in an inhalation device and subsequently inhaled by a patient so that the particles are able to reach the alveolar regions of the lungs.

A particular characteristic which relates directly to improved dispersibility and handling characteristics of respirable dry powders is rugosity. Rugosity is the ratio of the specific area (measured by molecular surface adsorption or another known technique) and the surface area calculated from particle size distribution (as measured by a centrifugal sedimentary particle size analyzer) and particle density (as measured by pycnometry), assuming non-porous spherical particles. If the particles are known to be generally nodular in shape, as spray dried particles are, rugosity is a measure of the degree of convolution or folding of the surface. A rugosity of 1 indicates that the particle is spherical and non-porous. Rugosity values greater than 1 indicate that the particle surface is non-uniform and convoluted to at least some extent, with higher numbers indicating a higher degree of non-uniformity. For the antibody-based powders of the present invention, it has been found that particles preferably have a rugosity of at least 2, more preferably of at least 3.

Prior dispersible dry powder formulations of macromolecules have shown that certain peptides and proteins could be formulated into dispersible dry powder compositions suitable for pulmonary delivery. However, the molecular weight of the peptides and proteins previously formulated is lower than the molecular weight of the antibodies formulated in the present invention, which have molecular weights of from about 150 to about 400 kilodaltons. It is well known that larger proteins are subject to degradation such as cleavage due to physical stress. Thus, they are not easily formulated into dispersible dry powders suitable for pulmonary delivery. Accordingly, it is unexpected that antibodies can be so formulated, as shown in the present invention.

The moisture content of the dry powder particles of the present invention is usually below about 10% by weight water, preferably below about 5% w and more preferably below about 3% w. Such low moisture content powders are generally physically and chemically stable during storage at room temperature and are readily dispersible in an inhalation device to form an aerosol.

Examples of antibodies which may be formulated using the present invention include those which have biological activity or which may be used to treat a disease or other condition. They include, but are not limited to, antibodies to microorganisms (including respiratory pathogens), monoclonal antibodies directed against tumor antigens and antibodies to cell receptors (including receptors involved in inflammation and allergy). Immunoconjugates of each of these examples may also be formulated using the present invention. Analogs, derivatives, fragments and pharmaceutically acceptable salts of the above may also be used. They may also be formulated with lipids, liposomes, microspheres or the like.

Antibodies suitable for use in the compositions of this invention include IgA, IgE, IgG, IgD and IgM. IgA, IgG and IgM antibodies are preferred, with IgG and IgA antibodies being particularly preferred. The amount of antibody which constitutes a therapeutically effective amount will vary in the composition depending on the biological activity of the antibody employed and the amount needed in the unit dosage form. The condition to be treated or prevented will also determine the amount of antibody required, as will the subject to which the antibody composition is being administered. Because antibodies are generally low potency drugs, the compositions comprise at least about 40% by weight antibody in the formulation, preferably between about 70% to about 100% and most preferably about 70% to about 90%. The amount of excipients and pharmaceutically acceptable carriers may be from about 0–60%, preferably from about 0–30% and most preferably from about 10–30% by weight.

Compositions according to the present invention comprise dispersible antibody powders intended for pulmonary delivery, i.e., inhalation by a patient into the alveolar regions of the patients lungs. The compositions comprise particles having an average particle size below about 10 μm. Preferably the particles of the composition will have a moisture content below about 10% by weight, more preferably below about 5% by weight and typically below about 3% by weight. Preferably at least about 50% by weight of the composition will comprise particles having a particle size less than about 5 μm, more preferably 75% of particles in the range from 0.4 μm to 5 μm. The compositions will often be packaged as unit doses where a therapeutically effective amount of the antibody composition is present in a unit dose receptacle, such as a blister pack, gelatin capsule, or the like, so long as a moisture barrier is provided.

Pharmaceutical excipients and/or additives useful in the present invention include proteins (e.g., HSA, recombinant human albumin (rHA), gelatin and casein), peptides (e.g., aspartame) and amino acids (e.g., alanine, glycine, arginine, glutamic acid and aspartic acid) which improve conformational stability of antibody during spray drying and also improve dispersibility of the powder. Carbohydrates/sugars and alditols are also particularly useful. Suitable carbohydrate/sugar compounds include sucrose, trehalose, lactose, raffinose, and the like. Suitable alditols include mannitol and pyranosyl sorbitol and the like. Polymeric excipients/additives include polyvinylpyrrolidones (PVP), Ficolls, soluble hydroxy ethyl starch, dextrates and the like of suitable molecular weight. Suitable pH adjusters or buffers include organic salts prepared from organic acids and bases, such as sodium citrate, glycine, sodium tartrate, sodium lactate, tromethamine and the like. Also useful are small amounts of pharmaceutically acceptable surfactants such as Tweens, chelators such as EDTA and inorganic acids and bases such as sodium phosphate and the like. Other suitable pharmaceutical excipients and/or additives include those disclosed in *Pharmaceutical Sciences,* Remington, 18th ed. (1990), the disclosure of which is incorporated herein by reference.

The antibody-based dry powder compositions of the present invention may be produced by spray drying solutions or slurries of the antibody and, optionally, excipients, in a solvent under conditions to provide a respirable dry powder. Solvents may include polar compounds such as water and ethanol, which may be readily dried. Antibody stability may be enhanced by performing the spray drying procedures in the absence of oxygen, such as under a nitrogen blanket or by using nitrogen as the drying gas.

Spray drying IgG with the optimized conditions described in the Examples section produced antibody-containing powders with particle size distribution between 1.2–1.8 μm MMD. The moisture content of these powders ranged from 1.3–3.5% by weight.

DISCLOSURE OF THE EXAMPLES OF THE INVENTION

The following examples are not intended to limit the scope of the invention in any manner.

Materials and Methods:

In general the following materials and methods were used in the examples that follow unless otherwise indicated.

Materials:

IgG, a glyocosylated protein of 150 kilodalton molecular weight purified from pooled normal human serum by fractionation on ion-exchange chromatography was purchased from Sigma. The IgG used was an essentially salt-free (less than 1% sodium), lyophilized bulk substance.

Formulation excipients were research grade or better. Citrate buffer salts used in formulation preparation were USP/ACS grade. The following excipients were used in preparing the IgG powders: Recombinant human serum albumin (Miles); Citric acid, monohydrate (JT Baker); Tri-sodium citrate, dihydrate (JT Baker); sucrose (EM Science); mannitol (USP); polyvinylpyrrolidone (PVP) k-15, molecular weight 10 kilodaltons (ISP Tech) and Ficoll (Pharmacia), a non-ionic synthetic polymer of sucrose, molecular weight 400 kilodaltons.

Analytical reagents used were reagent grade or better. Research grade dimethylformamide was used for moisture content analysis.

Sample Preparation and Handling:

Spray-dried powders were stored and prepared for analytical testing in a glove box maintained with dry air atmosphere. During powder transfer, the dry box was maintained at less than 5% relative humidity.

Physical Methods:

Moisture content

The water content of the powder formulations was determined by coulometric Karl Fischer titration using a Mitsubishi Model CA-06 moisture meter. A 5–10 mg aliquot of powder was dissolved in 1 ml of dimethylformamide (DMF). The sample was then injected into the titration cell of the moisture meter.

Powder particle size distribution

The particle size distribution (PSD) of the spray dried powder samples was measured with a Horiba CAPA-700 centrifugal sedimentation particle size analyzer. approximately 2–3 mg of powder was suspended in 2–3 ml of Sedisperse A-11 (Micromeritics, Norcross, Ga.) and sonicated briefly (5 minutes) before analysis. The instrument was configured to measure a particle size range of 0.4 to 10 μm in diameter (MMD). A particle density of 1.44 g/cm$^3$ was used for analyzing these powders.

Aerosol Methods:

Delivered dose assay

Delivered dose assay was performed to determine the efficiency and reproducibility of pulmonary delivery of the dispersible dry powder antibody composition. The device used was similar to devices disclosed in WO96/09085. The delivered dose was measured by collecting the aerosol on a filter placed over the mouthpiece of the chamber of the device. The powder sample was collected on a glass fiber filter (Gelman, 47 mm diameter) by drawing the aerosol from the chamber at an airflow of 30 L/minute for 2.5 seconds. Delivered dose efficiency was calculated by dividing the mass of the powder collected on the filter by the mass of the powder in the blister pack. Each result was the average of five replicate measurements.

Aerosol particle size distribution

The aerosol particle size distribution was obtained using an eight stage cascade impactor (Graseby Andersen, Smyrna, Ga.). The impactor air-flow was set to 28.3 L/min., the calibrated flow-rate for the instrument. For each run, 5 blister packs filled with approximately 5 mg of powder was dispersed from the inhaler. The particle size was determined by weighing the powder on the impactor plates and evaluating the results on a log-probability plot. Both the mass median aerodynamic diameter (MMAD) and the mass fraction less than 5 μm were determined from the log-probability plot.

The mass fraction of the aerosol powder less than 3.3 μm was obtained using a 2-stage (3.3 μm and 0.4 μm cut size) cascade impactor (short-stack Andersen). The impactor airflow was set to 28.3 L/minute, the calibrated operating flow rate of the instrument. For each measurement, one blister pack filled with a known weight of powder was dispersed from the inhaler. The resultant aerosol was drawn from the device chamber into the cascade impactor. The particle size fractions were determined by weighing the powder on the impactor filters. The % of mass <3.3 μm was determined based upon the weights of those filters.

Biophysical methods:

Attenuated Total Reflectance Fourier Transform—IR (ATR FT-IR)

Figure 1:
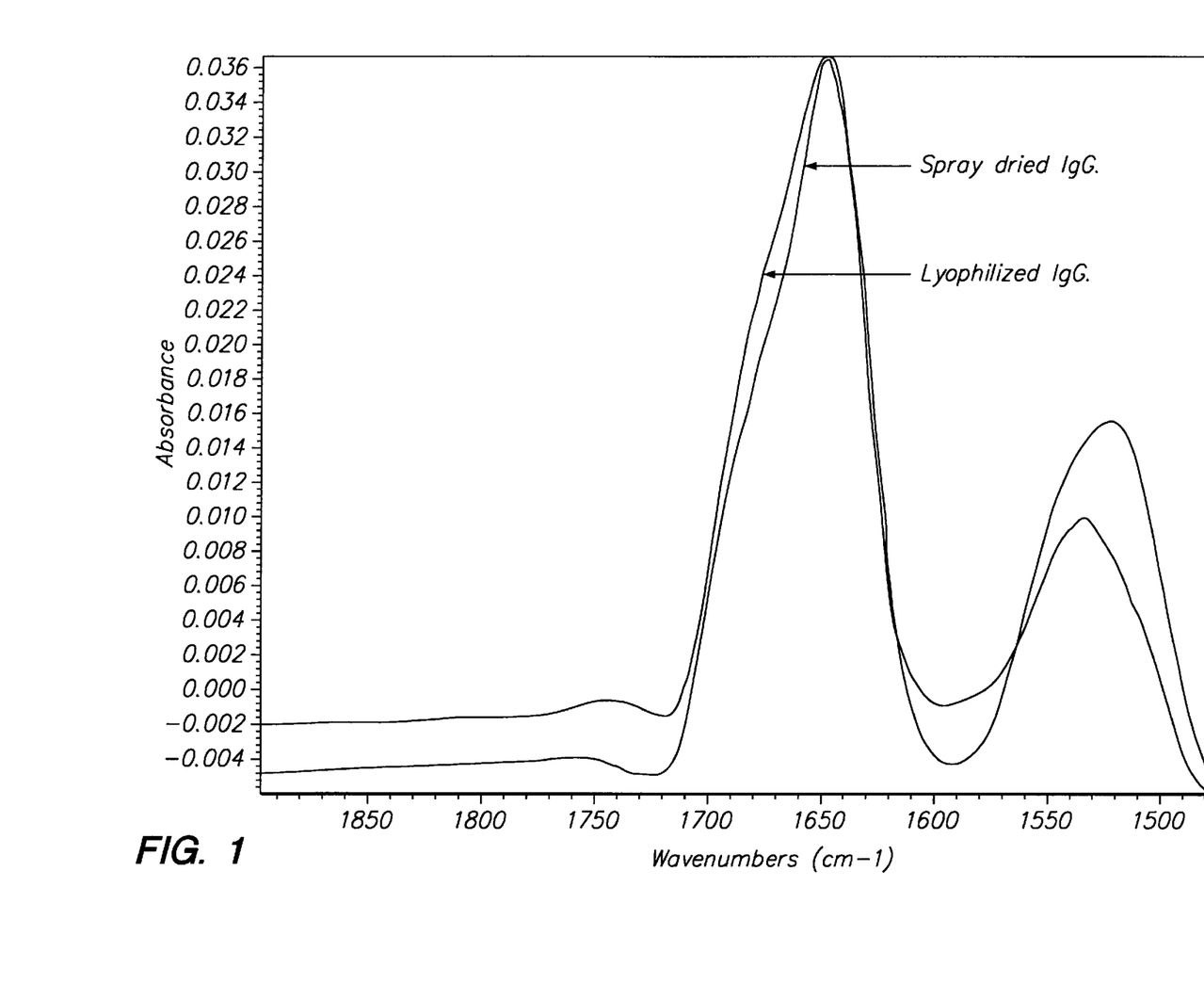
FIG. 1 illustrates comparative FT-IR spectra of spray dried and lyophilized 100% IgG. This figure shows that the spray dried powder retained antibody integrity.
Figure 2:
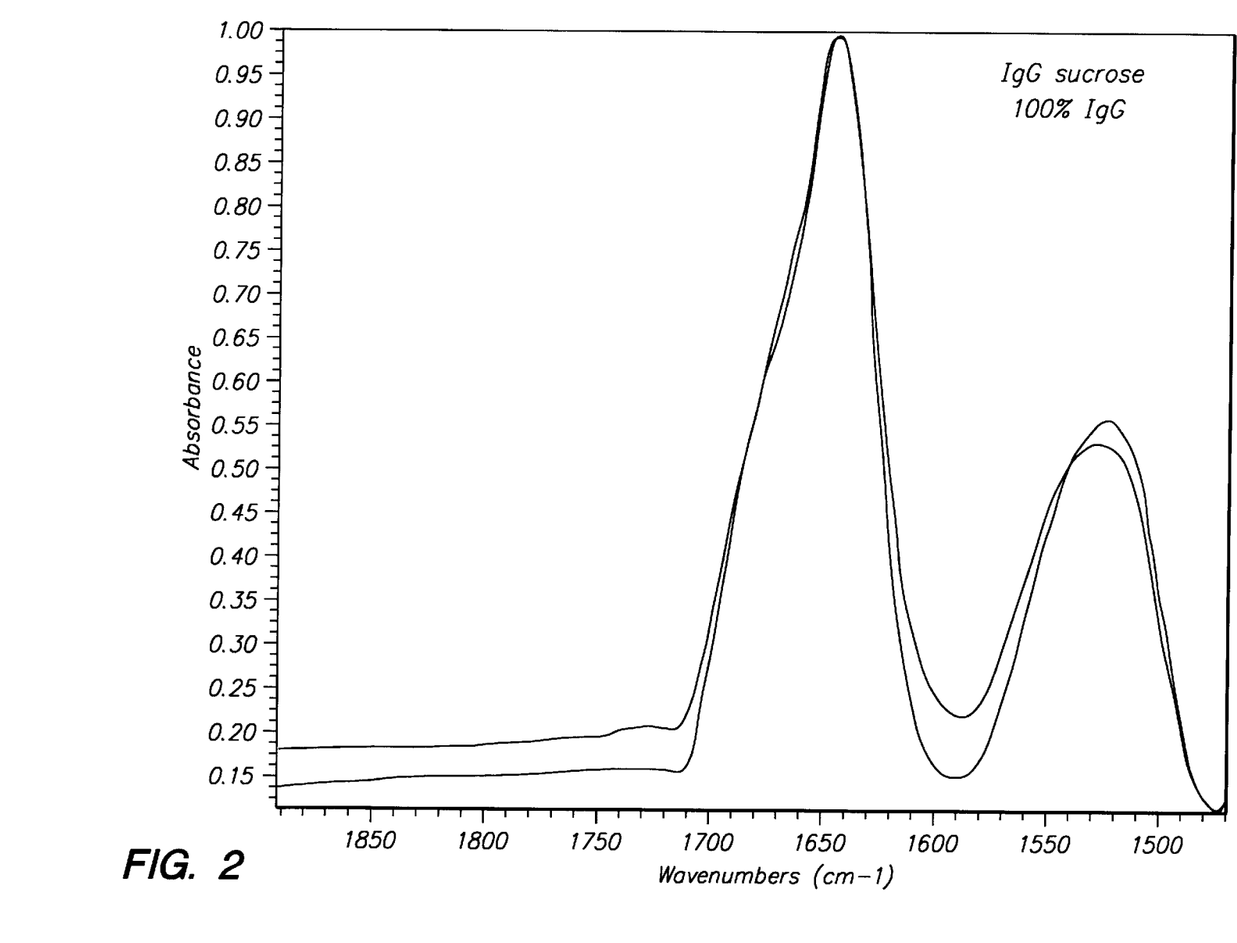
FIG. 2 illustrates comparative FT-IR spectra of 100% IgG and IgG:sucrose:citrate (70:20:10) powders, both of which retained native conformation.

Infrared (IR) spectroscopy can provide information regarding the secondary structure of proteins. The majority of the protein structural information, however, has been obtained from one absorbance originating primarily from the amide C=O stretching vibration: the amide I band. The sensitivity to variations in both geometric arrangements of atoms and hydrogen bonding enables infrared spectroscopy to discriminate between the various secondary structures incorporated within the three-dimensional organization of peptides and proteins, e.g., helical, extended sheet, disordered and turns. Solid samples, e.g., powders, which are not transparent are analyzed using ATR-IR. The basis for ATR-IR is that the IR beam enters an optically transparent medium, in this case Germanium crystal, on which the sample is layered. Comparison FT-IR spectra of spray dried and lyophilized powders were analyzed for differences which would indicate conformational changes due to spray drying. FIG. 1 shows the FT-IR spectra of lyophilized IgG and spray dried IgG. No significant difference in the spectra shape or peak maxima were noted, indicating that the spray dried IgG powder retained its conformational integrity. FIG. 2 shows that both a 100% IgG powder formulation and an IgG:sucrose:citrate (70:20:10) powder retained native conformation of antibody.

Intrinsic Tryptophan Fluorescence

Figure 3:
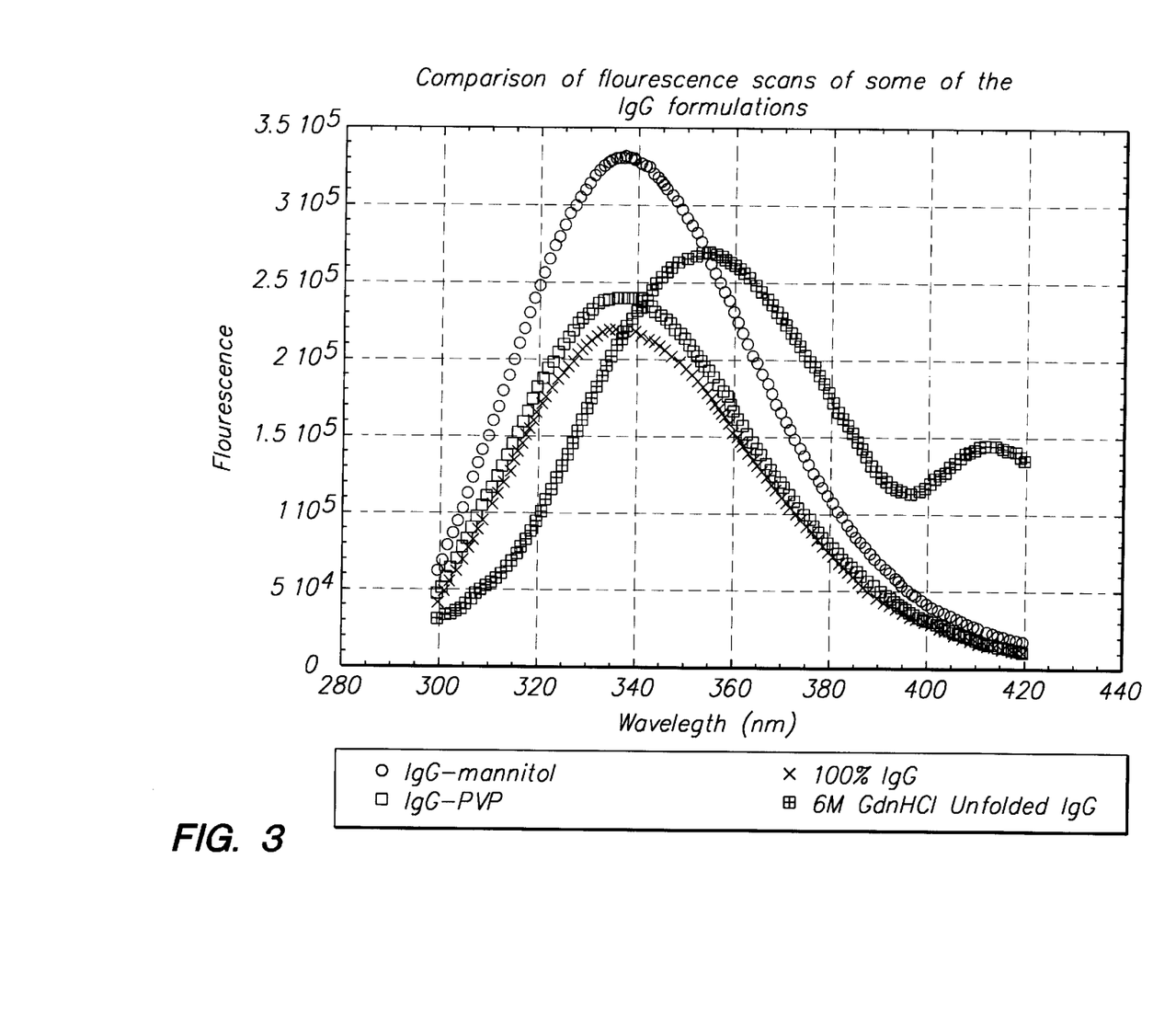
FIG. 3 is a fluorescence scan of some antibody powders of the present invention. No alteration in antibody conformation after spray drying was seen.

For most proteins, aromatic amino acid residues like tryptophan, tyrosine and phenylalanine contribute to the intrinsic fluorescence when excited at 280 nm. The intrinsic fluorescence in proteins is strongly dependent on the local environment of these fluorophores. A shift in the fluorescence maximum to a longer wavelength is observed when the environment changes from non-polar to polar. Antibodies, which have tryptophan residues in a relatively non-polar environment in the native state, have a fluorescence maximum at 337 nm which is shifted to 350 nm upon unfolding of the protein. The intrinsic fluorescence of reconstituted antibody powder formulations were measured using a SPEX-fluoromax fluorescence spectrophotometer. The samples were excited at 280 nm and fluorescence maxima measured. FIG. 3 shows fluorescence scans of reconstituted IgG: mannitol: citrate (70:20:10), IgG:PVP:citrate (70:20:10) and 100% IgG powders and a solution of IgG which had been unfolded by the denaturant guanidinium HCL. The scans of the reconstituted powder formulations show no shift in wavelength, indicating no unfolding of antibody. In contrast, the scan of the denatured IgG solution shows a wavelength shift indicative of unfolding.

UV turbidity assay

Figure 4:
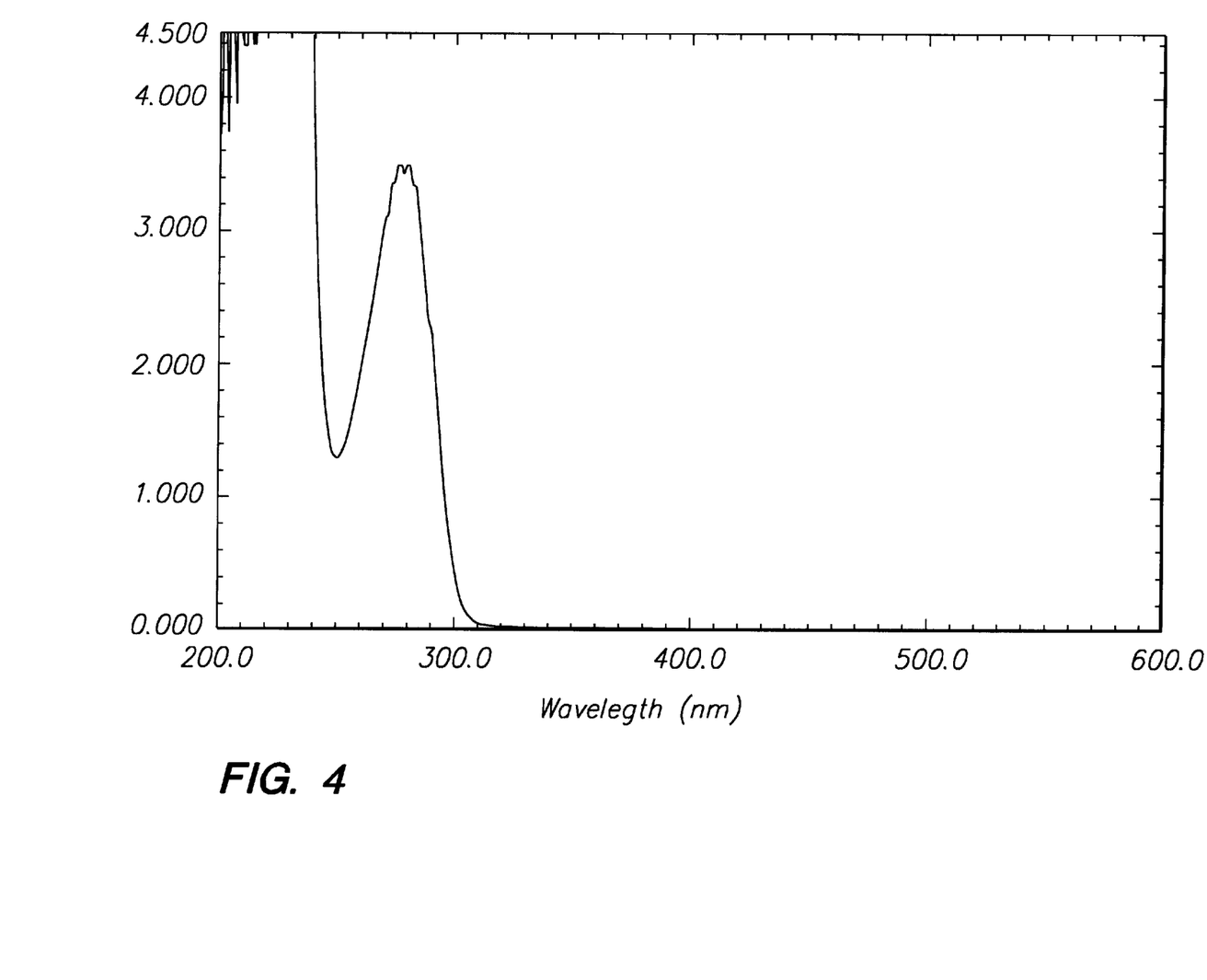
FIG. 4 illustrates a UV spectrum of an IgG:mannitol:citrate (70:20:10) powder after reconstitution. No light scattering at 400 nm was seen, indicating the absence of aggregation.

The UV turbidity assay was carried out to monitor physical stability of the protein and also to determine the yield upon reconstitution of the dry-powder in water. Suitable formulations must reconstitute in water without turbidity. The absorbance at 400 nm is a measure of the extent of aggregation (insoluble aggregates) in the solution. FIG. 4 shows that no aggregation was seen with an IgG: mannitol: citrate (70:20:10) formulation.

Dynamic Light Scattering (DLS)

Dynamic Light Scattering (DLS) measures light scattered from particles based on Brownian motion, the interaction of particles with solvent molecules. The instrument (Malvern Instruments) detects the fluctuation of light intensity using a digital correlator. The correlation functions are fitted into an analytical program to calculate the particle size distribution. DLS was used to measure soluble aggregates in reconstituted antibody powder formulations. Samples of individual blister packs were combined to give approximately 2–4 mg of powder per ml. These samples were reconstituted in water and centrifuged at 10,000 rpm for 5 minutes to remove any dust particles, which interfere with readings. The samples were decanted and placed in a cylindrical quartz cell for analysis. A semi-quantitative method of particle size determination by light intensity was developed, using a multi-modal method of data analysis supplied by Malvern Instruments. Measurements were taken at a range of angles from 75° to 120°. Larger particles are more easily detectable at smaller angles, while smaller particles are more readily detected at larger angles. The IgG monomer has been reported to have a diameter of 11 nm, as measured by DLS (Singh et al., Biopolymers 31: 1387–1396 (1991)).

SEC-HPLC

SEC-HPLC was used to measure soluble aggregates in reconstituted antibody powder formulations. An HPLC system equipped with a TSK-3000 column was used. The mobile phase consisted of 0.05M $KH_2PO_4$ buffer (pH 6.8), 0.1 M KCl and 0.0015 M $NaN_3$. The assay results were obtained by determining the relative area for each peak in the chromatogram for spray dried material relative to lyophilized material. Preferred formulations showed less than 5% aggregates by SEC-HPLC.

SDS-PAGE

Silver stain SDS-PAGE analysis was used to evaluate reconstituted powder formulations for covalent aggregates of the antibodies and to confirm SEC-HPLC methods. SDS-PAGE analysis was carried out using a Pharmacia Phast system consisting of discontinuous 8 to 25% gradient Phast gels. Spray dried antibody powder formulations were reconstituted with purified water, then further diluted with SDS-PAGE buffer to an antibody concentration of 1 mg/ml. Samples were incubated in 10% SDS non-reducing sample buffer at 37° C. for 30 minutes, then 4 µg samples were loaded into each well. The gels were run and silver stained using Pharmacia standard procedures for 8 to 25% SDS-PAGE gels.

Formulation preparation:

A 100% formulation of antibody was prepared by dissolving 5 mg of IgG in 1.0 ml of deionized water. The pH of the protein solution was measured to be about 6.5.

A 90% formulation of antibody was prepared by dissolving 4.5 mg of IgG in 1.0 ml of 2mM citrate buffer. The pH of the protein solution was measured, and was generally found to be about 6.5.

A 70% formulation of antibody was prepared by dissolving 3.5 mg of antibody and 1 mg/ml of excipient in 1.0 ml of 2 mM citrate buffer. The pH of the protein solution was measured to be about 6.5.

The various classes of excipients used were as follows:

Sugar excipients: sucrose, lactose, mannitol, raffinose and trehalose.

Polymeric excipients: Ficoll and PVP.

Protein excipients: HSA.

Powder processing:

Dry powders of the above formulations were produced by spray drying using a Buchi Spray Dryer using the following parameters:

| | |
|---|---|
| Temperature of the solution | 4–6° C. |
| Inlet temperature | 98–105° C. |
| Feed rate | 5.0 ml/min. |
| Outlet temperature | 64–67° C. |
| Atomizer pressure | 40 psi |
| Cyclone coolant temperature | 30° C. |

Once the aqueous mixture was consumed, the outlet temperature was maintained at 67° C. for 10 minutes by slowly decreasing the inlet temperature to provide secondary drying.

Process suitability was assessed by evaluating the antibody powders for moisture content, particle size distribution, delivered dose, aerosol efficiency and antibody integrity.

Before preparing the antibody powders, solution formulations were analyzed to demonstrate that the protein is stable in solution over the process period during spray-drying. The antibody solutions were atomized to investigate protein aggregation in the high shear of the pneumatic atomizer. The protein stability was assayed by UV and SEC-HPLC. The absence of insoluble protein aggregates as determined by UV in the 350–400 nm region of the spectrum indicated that antibody did not aggregate or precipitate during atomization.

EXAMPLE 1

100% IgG Formulation for Pulmonary Delivery

Bulk lyophilized IgG was formulated and spray dried as described above. The 100% IgG dry powder was analyzed for moisture as described above and found to contain 2.5–3.5% moisture.

The particle size distribution was measured by centrifugal sedimentation as described above and was determined to be 1.3 μm to 1.5 μm MMD. The delivered dose of the IgG powder composition was measured as described above and was determined to be 60 to 62% of the total powder (5.0 mg) loaded into the device. The aerosol particle size distribution, measured as described above was determined to be 4.1 μm MMAD, with 61.6% of the particles <5.0 μm in diameter.

The antibody integrity was assayed by SEC-HPLC and dynamic light scattering (DLS) as described above. The powder did not reconstitute easily in water (47% reconstitution), so no UV measurement was possible. The mean diameter of particles was found to be 18 nm by DLS. The size distribution indicated the presence of a small population of soluble aggregates. We found 7.5% soluble aggregates by SEC-HPLC in the reconstituted spray dried sample. ATR FT-IR and intrinsic fluorescence assays, performed as described above, indicated no conformational change in antibody from spray drying. SDS-PAGE results showed the presence of covalent aggregates.

EXAMPLE 2

90% IgG Formulation for Pulmonary Delivery

Bulk lyophilized IgG was formulated and spray dried as described above. The 90% IgG dry powder composition contained 90% IgG and 10% citrate. The formulation contained 2–2.5% moisture.

The particle size distribution was determined by centrifugal sedimentation to be 1.3 μm to 2.0 μm MMD, with 98% of the particles less than 5 μm. The delivered dose of the IgG powder was determined to be 46% of the total powder (5.0 mg) loaded into the device. The aerosol particle size distribution was determined to be 1.5 μm MMAD, with 99% of the particles <5.0 μm in diameter.

The powder gave about 66% reconstitution in water. The antibody integrity was assayed by SEC-HPLC. About 15% of soluble aggregates was detected in the reconstituted sample after spray-drying. The fluorescence maximum for the reconstituted sample was around 337 nm, indicating no alteration in antibody conformation after spray drying.

EXAMPLE 3

70% IgG Formulation Containing Carbohydrate Excipient

Bulk lyophilized IgG was formulated and spray dried as described above. A 70% formulation was achieved by dissolving 3.5 mg of IgG and 1 mg sucrose in 1.0 ml of 2 mM citrate buffer. The 70% IgG dry powder composition contained 70% IgG, 20% sucrose and 10% citrate. The pH of the resulting solution was determined to be about 6.5. The formulation contained 2–2.5% moisture.

The particle size distribution was determined by centrifugal sedimentation to be 1.0 μm to 1.5 μm MMD, with 97% of the particles less than 5 μm. The delivered dose of the IgG powder was determined to be 45 to 52% of the total powder (5.0 mg) loaded into the device. The aerosol particle size distribution was determined to be 3.2 μm MMAD, with 67% of the particles <5.0 μm in diameter and 45% under 3.3 μm.

The antibody integrity was assayed by UV and SEC-HPLC. The powder reconstituted well, with complete recovery of antibody and absence of aggregates as shown by UV. About 3–4% of soluble aggregates were detected by SEC-HPLC in the reconstituted sample after spray-drying. The fluorescence maximum for the reconstituted sample was around 337 nm, indicating no alteration in antibody conformation after spray drying.

EXAMPLE 4

70% IgG Formulation Containing Polymeric Excipient

Bulk lyophilized IgG was formulated and spray dried as described above. A 70% formulation was achieved by dissolving 3.5 mg of IgG and 1 mg of PVP in 1.0 ml of 2 mM citrate buffer. The pH of the protein solution was measured to be at 6.7. The 70% IgG dry powder composition contained 70% IgG, 20% PVP and 10% citrate. The formulation contained 1.5–2% moisture.

The particle size distribution was determined by centrifugal sedimentation to be 1.7 μm to 2.0 μm MMD, with 97% of the particles less than 5 μm. The delivered dose of the IgG powder was determined to be 62% of the total powder (5.0 mg) loaded into the device. The aerosol particle size distribution showed that 41% of the particles were <3.3 μm in diameter.

Antibody integrity was assayed by UV. The absence of insoluble protein aggregates as determined by UV in the 350–400 nm region of the spectrum indicated that IgG did not aggregate or precipitate during spray-drying. The fluorescence maximum for the reconstituted sample was around 337 nm, indicating no alteration in antibody conformation after spray drying.

EXAMPLE 5

70% IgG Formulation with Protein Excipient

Bulk lyophilized IgG was formulated and spray dried as described above. A 70% formulation was achieved by dissolving 3.5 mg of IgG and 1 mg HSA (Miles-Pentex) in 1.0 ml of 2 mM citrate buffer. The pH of the protein solution was measured to be at 6.2. The 70% IgG dry powder composition contained 70% IgG, 20% HSA and 10% citrate. The formulation contained 2.8–3.3% moisture.

The particle size distribution was determined by centrifugal sedimentation to be 1.3–1.5 μm MMD, with 100% of the particles less than 5 μm. The delivered dose of the IgG powder was determined to be 70 to 75% of the total powder (5.0 mg) loaded into the device. The aerosol particle size distribution was determined to be 3.8 μm MMAD, with 68% of the particles <5.0 μm in diameter.

Antibody integrity was assayed by UV and SEC-HPLC. The powder did not reconstitute easily, with only about 35% recovered after reconstitution based on UV analysis. About 9% of soluble aggregates was determined by SEC-HPLC. No fluorescence determination was performed, due to interference that would result from the presence of another protein, i.e., HSA.

EXAMPLE 6

90% IgG Formulation with Surfactant Excipient

Bulk lyophilized IgG was formulated and spray dried as described above. A 90% formulation was achieved by dissolving 4.5 mg of IgG in 1.0 ml of 2 mM citrate buffer containing 0.05% BAC. The pH of the protein solution was measured to be at 6.5. The above 90% IgG dry powder composition contained 89.95% IgG, 0.05% BAC and 10% citrate. The formulation contained 3–3.5% moisture.

The particle size distribution was determined by centrifugal sedimentation to be 1.4 μm MMD, with 100% of the particles less than 5 μm. The delivered dose of the IgG powder was determined to be 45% of the total powder (5.0 mg) loaded into the device. The aerosol particle size distribution was determined to be 3.6 µm MMAD, with 69% of the particles <5.0 µm in diameter.

The IgG-surfactant powder gave a turbid-looking solution upon reconstitution.

EXAMPLE 7

100% IgA Formulation

IgA obtained from Sigma was preformulated in 10 mM Tris and 100 mM NaCl, pH 7.4. It was dialyzed against de-ionized water overnight at 4° C. The dialyzed protein was concentrated using a filtron unit to 5 mg/ml. The pH of the resulting solution was determined to be 6.9. The solution was spray dried as described above. The 100% IgA dry powder contained 3–3.5% moisture.

The particle size distribution was determined by centrifugal sedimentation to be 1.22 µm MMD, with 97% of the particles less than 5 µm. The delivered dose of the IgA powder was determined to be 50–52% of the total powder (5.0 mg) loaded into the device.

Antibody integrity was assayed by UV and dynamic light scattering. The absence of insoluble protein aggregates as determined by UV in the 350–400 nm region of the spectrum indicated that IgA did not aggregate or precipitate during atomization.

EXAMPLE 8

70% IgA Formulation Containing Protein Excipient

IgA obtained from Sigma was preformulated in 10 mM Tris and 100 mM NaCl, pH 8.0. It was dialyzed against 2 mM citrate buffer, pH 6.5 overnight at 4° C. 40 mg of HSA (Miles Pentex) was dissolved in 30 ml of dialyzed IgA solution (4.16 mg/ml) and the resulting solution spray dried as described above. The 70% IgA dry powder composition contained 70% IgA, 20% HSA and 10% citrate. The formulation contained 2.6% moisture.

The particle size distribution was determined by centrifugal sedimentation to be 1.22 µm MMD, with 97% of the particles less than 5 µm. The delivered dose of the IgA powder was determined to be 65% of the total powder (5.0 mg) loaded into the device.

EXAMPLE 9

70% IgG Formulation Containing Carbohydrate Excipient

Bulk lyophilized IgG was formulated and spray dried as described above. A 70% formulation was achieved by dissolving 3.5 mg of IgG and 1 mg mannitol in 1.0 ml of 2 mM citrate buffer. The 70% IgG dry powder composition contained 70% IgG, 20% mannitol and 10% citrate. The pH of the resulting solution was determined to be about 6.5. The formulation contained 1.7% moisture.

The particle size was determined by centrifugal sedimentation to be 1.9 µm MMD, with 100% of the particles less than 5 µm. The delivered dose of the IgG powder was determined to be 53% +4% of the total powder (5.0 mg) loaded into the device. The aerosol particle size distribution showed that 45% of the particles were <3.3 µm in diameter.

The antibody integrity was assayed by UV and SEC-HPLC. The powder reconstituted well, with complete recovery of antibody and absence of aggregates as shown by UV. About 3–4% of soluble aggregates were detected by SEC-HPLC in the reconstituted sample after spray-drying. The fluorescence maximum for the reconstituted sample was around 337 nm, indicating no alteration in antibody conformation after spray drying. SDS-PAGE results showed the presence of covalent aggregates.

EXAMPLE 10

70% IgG Formulation Containing Polymeric Excipient

Bulk lyophilized IgG was formulated and spray dried as described above. A 70% formulation was achieved by dissolving 3.5 mg of IgG and 1 mg of Ficoll-400 in 1.0 ml of 2 mM citrate buffer. The pH of the protein solution was measured to be at 6.7. The 70% IgG dry powder composition contained 70% IgG, 20% Ficoll and 10% citrate. The formulation contained 1.9% moisture.

The particle size distribution was determined by centrifugal sedimentation to be 1.78 µm MMD, with 100% of the particles less than 5 µm. The delivered dose of the IgG powder was determined to be 62% of the total powder (5.0 mg) loaded into the device.

EXAMPLE 11

Effect of Excipients on DDE of Spray Dried IgG Powders

The delivered dose efficiency (DDE) of the spray dried IgG powders varied considerably, depending on the type of excipient used. The 100% IgG powders showed a delivered dose efficiency of about 60%. The use of sugars as excipients decreased the delivered dose efficiency to about 40–55%. Addition of polymeric excipients such as Ficoll and PVP did not alter the delivered dose efficiency (with respect to the 100% IgG). Results are presented in Table 1.

HSA is a commonly used protein excipient for parenteral delivery. An increase in the delivery efficiency of powders of small molecules and proteins upon addition of HSA has been observed. Addition of HSA to the solutions used to form spray dried IgG powders resulted in an increase in the DDE, although the increase seemed to be independent of the HSA concentration (5–20%). The mass median aerodynamic diameters (MMAD) ranged from 2.5–4 µm for all powders tested.

TABLE 1

Effect of Excipients on DDE of Spray Dried IgG Powders

| Powder Formulation | Delivered Dose Efficiency | Relative Standard Deviation |
|---|---|---|
| 100% IgG | 60 | 8 |
| 100% IgG | 62 | 1 |
| 90% IgG, 10% Citrate | 37 | 7 |
| 90% IgG, 10% Citrate | 44 | 9 |
| 70% IgG, 20% Sucrose, 10% Citrate | 53 | 6 |
| 40% IgG, 20% Sucrose, 10% Citrate | 52 | 5 |
| 70% IgG, 20% Mannitol, 10% Citrate | 53 | 4 |
| 70% IgG, 20% Trehalose, 10% Citrate | 49 | 7 |
| 70% IgG, 20% PVP, 10% Citrate | 63 | 3 |
| 70% IgG, 30% Citrate | 48 | 18 |
| 70% IgG, 20% Lactose, 10% Citrate | 48 | 5 |
| 70% IgG, 20% Raffinose, 10% Citrate | 42 | 4 |
| 70% IgG, 20% Ficoll 400, 10% Citrate | 62 | 6 |
| 70% IgG, 20% HSA, 10% Citrate | 70 | 5 |
| 70% IgG, 30% HSA | 75 | 2 |
| 70% IgG, 20% HSA, 10% Citrate | 71 | 6 |
| 70% IgG, 20% HSA, 10% Citrate | 73 | 10 |
| 85% IgG, 15% HSA | 79 | 5 |

TABLE 1-continued

Effect of Excipients on DDE of Spray Dried IgG Powders

| Powder Formulation | Delivered Dose Efficiency | Relative Standard Deviation |
|---|---|---|
| 95% IgG, 5% HSA | 80 | 1 |
| 85% IgG, 15% HSA | 77 | 4 |
| 85% IgG, 15% HSA | 79 | 2 |
| 85% IgG, 15% HSA | 71 | 7 |
| 95% IgG, 5% HSA | 76 | 5 |

EXAMPLE 12

Rugosity of Antibody Powders

The rugosity of certain dry powder antibody compositions of the present invention is presented in Table 2. Results showed that all antibody powders and a powder composed of 100% HSA had rugosity of at least 2.

TABLE 2

Rugosity of Antibody Powders

| Powder Formulation | Rugosity | DDE |
|---|---|---|
| 100% IgG | 2.02 | 60 |
| IgG + Citrate | 2.40 | 51 |
| 100% HSA | 3.37 | 81.4 |
| IgG + HSA | 2.93 | 75.3 |

Modification of the above-described modes of carrying out the various embodiments of this invention will be apparent to those skilled in the art following the teachings of this invention as set forth herein. The examples described above are not limiting, but are merely exemplary of this invention, the scope of which is defined by the following claims.

The disclosure of each publication, patent or patent application mentioned in this specification is hereby incorporated by reference to the same extent as if each individual publication, patent or patent application were specifically and individually indicated to be incorporated by reference.

We claim:

1. An IgG antibody-based dry powder composition for pulmonary delivery comprising a predetermined amount of IgG antibody which is non-aggregated and is in its native conformation in respirable dry powder particles having a particle size less than 10 micrometers wherein said composition has a delivered dose efficiency of at least about 30%.

2. The composition of claim 1 which is dispersible.

3. The composition of claim 1 which further comprises a pharmaceutically acceptable excipient or carrier.

4. The composition of claim 3 wherein the carrier or excipient is selected from the group consisting of sugars, alditols, organic salts, amino acids, polymers, proteins and peptides.

5. The composition of claim 1 wherein the IgG antibody comprises at least about 40% by weight of the composition.

6. The composition of claim 1 wherein the particles in the powder have a particle size range of from about 0.4 μm to about 5 μm MMD.

7. The composition of claim 1 wherein the particles have an MMAD of less than about 5 μm.

8. The composition of claim 1 which contains less than about 10% by weight moisture.

9. A method for preparing the composition of claim 1 comprising:

a) mixing the IgG antibody with a solvent to form a solution or suspension; and b) spray drying the mixture formed in step a) under conditions which provide a respirable dry powder, wherein the IgG antibody is non-aggregated, is in its native conformation and wherein the resulting composition has a delivered dose efficiency of at least about 30%.

10. The method of claim 9 further comprising the step of adding a pharmaceutically acceptable excipient or carrier prior to spray drying.

11. The method of claim 9 wherein the solvent is selected from the group consisting of water and ethanol.

12. A method of treating or preventing a condition in an animal which may be prevented or alleviated by an IgG antibody, the method comprising pulmonary administration of a therapeutically effective amount of the composition of claim 1 to an animal susceptible to or suffering from the condition.

13. The method of claim 12 wherein the condition is selected from the group consisting of inflammation, allergy, cancer, bacterial infection and viral infection.

* * * * *